United States Patent [19]

Watson et al.

[11] Patent Number: 4,492,675

[45] Date of Patent: Jan. 8, 1985

[54] APPARATUS FOR THE PRODUCTION OF VINYLTOLUENE

[75] Inventors: James M. Watson, Big Spring, Tex.; Darrell E. Bailey, Prairieville, La.

[73] Assignee: Cosden Technology, Inc., Dallas, Tex.

[21] Appl. No.: 316,446

[22] Filed: Oct. 29, 1981

Related U.S. Application Data

[62] Division of Ser. No. 221,662, Dec. 31, 1980.

[51] Int. Cl.³ .................. B01D 3/34; C07C 7/05; C07C 7/20
[52] U.S. Cl. .................. 422/187; 202/173; 203/9; 422/189; 585/440
[58] Field of Search .................. 585/440–445, 585/808; 422/134, 187–189; 203/3, 9, 61, 65, 84; 202/173

[56] References Cited

U.S. PATENT DOCUMENTS

| | | | |
|---|---|---|---|
| 2,443,217 | 6/1948 | Amos et al. | 585/440 |
| 2,775,629 | 12/1956 | Anderson, Jr. | 585/440 X |
| 3,426,091 | 2/1969 | Miron et al. | 585/440 |
| 3,629,076 | 12/1971 | Jones | 585/440 X |
| 3,702,346 | 11/1972 | Kellar | 585/440 |
| 4,033,829 | 7/1977 | Higgins, Jr. et al. | 203/9 |
| 4,132,601 | 1/1979 | Watson | 203/61 X |
| 4,182,658 | 1/1980 | Watson | 203/9 |
| 4,191,614 | 3/1980 | Watson et al. | 203/9 X |
| 4,252,615 | 2/1981 | Watson | 585/808 X |
| 4,417,084 | 11/1983 | Chu | 585/440 |

FOREIGN PATENT DOCUMENTS

| | | | |
|---|---|---|---|
| 594343 | 3/1960 | Canada | 585/440 |
| 51-43727 | 4/1976 | Japan | 203/9 |

Primary Examiner—Richard L. Chiesa
Attorney, Agent, or Firm—John K. Abokhair

[57] ABSTRACT

An apparatus for preparing vinyltoluene comprising passing ethyltoluene through a dehydrogenation zone to form vaporous crude vinyltoluene, adding from about 50 to about 100 parts per million by weight of a polymerization inhibitor such as a nitrated phenol to the vaporous crude vinyltoluene at a temperature between about 200° and about 300° C., condensing the vaporous crude vinyltoluene, maintaining the pH of the aqueous phase of the condensed crude vinyltoluene at a value between about 5.5 and about 6.5 sufficient to maintain the inhibitor in the organic phase of the condensed crude vinyltoluene, adding a second portion of polymerization inhibitor to the condensed crude vinyltoluene until the inhibitor concentration totals about 500 parts per million by weight relative to the vinyltoluene content of the crude vinyltoluene, filtering the condensed crude vinyltoluene to remove seed polymer, and distilling the condensed crude vinyltoluene to recover substantially pure vinyltoluene; and apparatus for carrying out said method.

14 Claims, 2 Drawing Figures

APPARATUS FOR THE PRODUCTION OF VINYLTOLUENE

This is a division of application Ser. No. 221,662, filed Dec. 31, 1980.

BACKGROUND OF THE INVENTION

The present invention pertains to an apparatus for the production of vinyltoluene, and more specifically to a means for inhibiting the formation of undesirable thermal polymers in the manufacture of vinyltoluene.

Vinyltoluene is commonly prepared by the catalytic dehydrogenation of ethyltoluene, cooling of the gaseous materials to condense the same and fractionally distilling the liquid product to obtain vinyltoluene. In the manufacture of vinyltoluene by the catalytic dehydrogenation of ethyltoluene, considerable difficulty has been experienced prior to and during the distillation of the crude vinyltoluene product to obtain purified vinyltoluene, because of the production of thermal polymers. This problem manifests itself in a plugging of the equipment used for the manufacture of the vinyltoluene.

In order to prevent the formation of the thermal polymer during distillation of vinyltoluene, various types of known polymerization inhibitors have been employed in connection with prior art distillation processes. These inhibitors have been only partially effective in preventing the formation of the undesirable thermal polymer in the distillation apparatus. However, since this normal addition of inhibitor to the crude vinyltoluene product takes place in or just prior to the distillation apparatus, the inhibitor does not prevent the formation of the undesirable thermal polymers in the equipment upstream of the distillation unit, such as in the condensers and in the crude vinyltoluene drum. The occurrence of fouling in the condensers and drum due to polymer formation represents a serious problem in the production of vinyltoluene.

SUMMARY OF THE INVENTION

It is therefore an object of the present invention to provide an improved process for the production of vinyltoluene.

Another object of the invention resides in the provision of a method for preventing the formation of soluble and insoluble (cross-linked) thermal polymers during the processing and subsequent distillation of vinyltoluene feed stock prepared by the catalytic dehydrogenation of ethyltoluene.

It is a particular object of the present invention to provide a new and improved process for preventing the fouling of the crude vinyltoluene condensers and drums used prior to distillation with undesirable thermal polymers.

A further object of the present invention is to provide a new and improved apparatus which is less prone to fouling with thermal polymers during the manufacture of vinyltoluene.

In accomplishing the foregoing objects, there has been provided in accordance with the present invention a process for the production of vinyltoluene comprising the steps of passing ethyltoluene through a dehydrogenation zone to form vaporous crude vinyltoluene; adding a first portion of polymerization inhibitor to the vaporous crude vinyltoluene; condensing the vaporous crude vinyltoluene; maintaining the pH of the aqueous phase of the condensed crude vinyltoluene at a value sufficient to maintain the inhibitor in the organic phase of the condensed crude vinyltoluene; adding a second portion of polymerization inhibitor to the condensed crude vinyltoluene; and distilling the condensed crude vinyltoluene under distillation conditions to recover pure vinyltoluene. The condensed crude vinyltoluene may advantageously be filtered before distillation to remove polymer which may otherwise serve as "seed" polymer in the distillation train. The polymerization inhibitor may comprise a nitrated phenol, preferably dinitro-para-cresol (DNPC).

In accordance with a further aspect of the invention, the pH of the aqueous phase is adjusted to a level of from about 5.5 to about 6.5. Additionally, the process may further comprise the step of recycling the aqueous phase back to the dehydrogenation step.

In accordance with a still further aspect of the invention, the first portion of polymerization inhibitor is added when the vaporous crude vinyltoluene temperature is from about 200° C. to about 300° C. Also, the first portion of polymerization inhibitor is advantageously added in amounts of about 50 to 100 parts per million by weight relative to the vinyltoluene present, and the total of the first and second portions of the inhibitor added is preferably sufficient to bring the inhibitor concentration to a level of about 500 parts per million during the distillation step.

In accordance with still another aspect of the present invention, there is provided an apparatus for manufacturing vinyltoluene, comprising means for dehydrogenating ethyltoluene to form vaporous vinyltoluene; first means for introducing a polymerization inhibitor into the vaporous vinyltoluene after the vaporous vinyltoluene leaves the dehydrogenation means; means for condensing the vaporous vinyltoluene; means for collecting the condensed vinyltoluene; a second means for introducing a polymerization inhibitor into the collected vinyltoluene; and means for purifying the vinyltoluene, preferably a distillation apparatus. Additionally, a filter for filtering the vinyltoluene may be included prior to the purification thereof.

In the process according to the invention, a portion of the inhibitor is introduced directly into the stream of vaporous vinyltoluene as it leaves the dehydrogenation apparatus but immediately prior to its condensation. The pH required to maintain the inhibitor in the organic phase of the vinyltoluene feed stock will vary depending upon the pKa of the inhibitor selected. It has been found that the pH required for DNPC is less than about 6.5 and typically between about 5.5 and about 6.5. However, if inhibitors other than DNPC are used during the processes, the pH required to maintain the inhibitor in the organic phase will depend on the acidic character of the inhibitor employed during the process. Any conventional filter may be utilized to filter the crude vinyltoluene feed stock prior to distillation. It has been found that a filter with passages of less than about 50 microns is the most efficient size in removing any undesirable thermal polymer.

Through the use of the process according to the present invention, the amount of polymerization occurring before and during the distillation of vinyltoluene is significantly reduced in comparison to conventionally employed methods. In addition, the amount of desired distillation product is increased in proportion to the decrease in the amount of polymer formation. Still further, since the inhibitor is maintained in the organic phase of the vinyltoluene, the water can be reused, e.g., in the generation of dilution steam for dehydrogenating ethyltoluene.

Other objects, features and advantages of the invention will become apparent from the detailed description of the preferred embodiments which follows, when considered together with the attached figures of drawing.

DETAILED DESCRIPTION OF PREFERRED EMBODIMENTS

Figure 1:
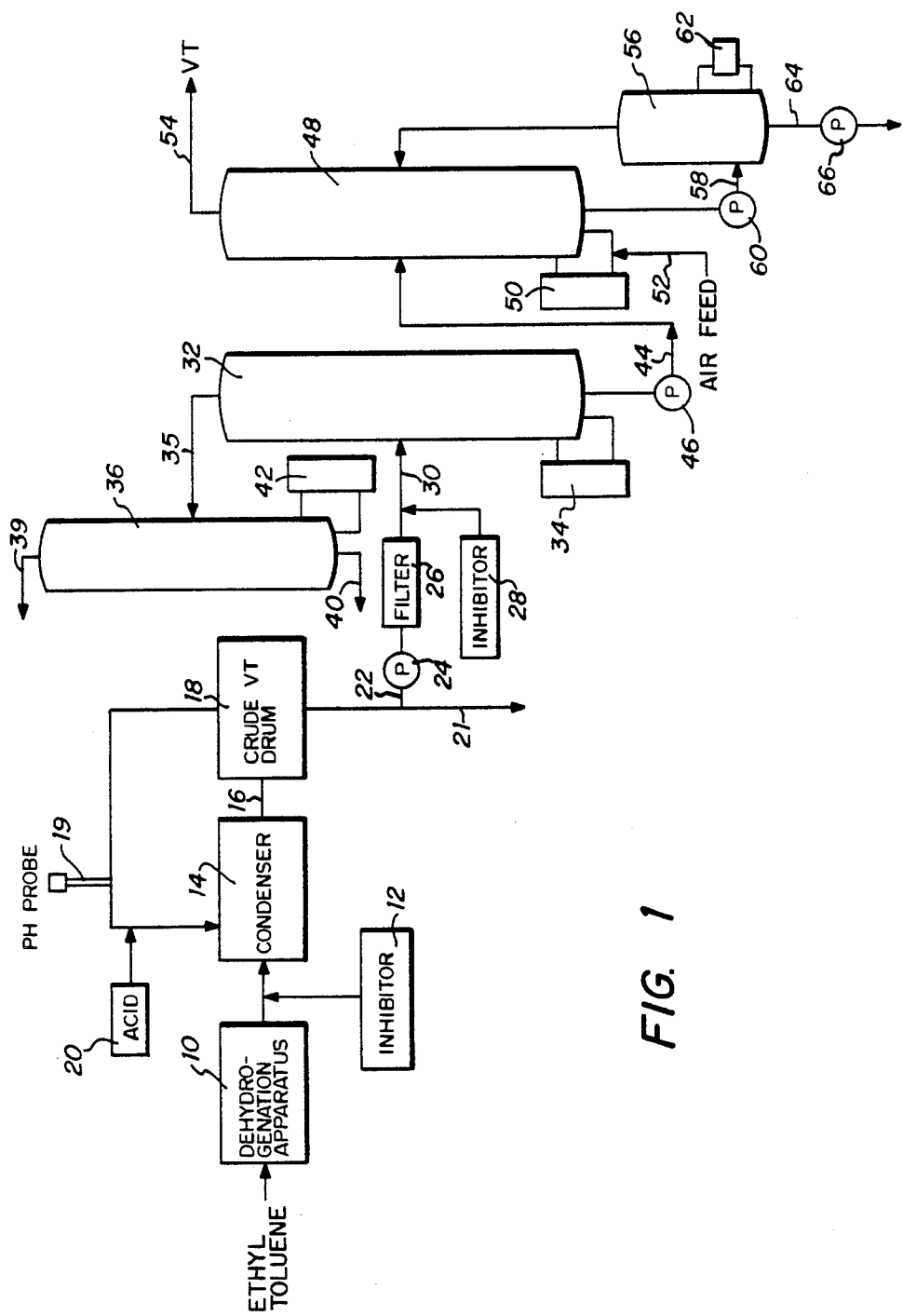
FIG. 1 is a schematic diagram of a preferred embodiment of the apparatus employed in practicing the present invention.

Vinyltoluene is typically manufactured by reacting toluene with ethylene in the presence of an activated Friedel-Crafts catalyst, such as aluminum chloride, or a zeolite catalyst, dehydrogenating the ethyltoluene by passing it together with steam through a dehydrogenation zone at a sufficient reaction temperature, and separating the dehydrogenated product by means of fractional distillation.

The present invention provides a process and apparatus for the production of vinyltoluene whereby the formation of the undesirable thermal polymer can be greatly inhibited or entirely prevented prior to and during distillation of vinyltoluene feed stock prepared by the catalytic dehydrogenation of ethyltoluene. This is accomplished by adding an inhibitor immediately prior to the step of condensing the dehydrogenated vinyltoluene feed stock, adjusting the pH of the aqueous phase of the condensed feed stock to maintain the inhibitor substantially in the organic phase, and optionally filtering the feed stock prior to fractional distillation.

Toluene is alkylated to form ethyltoluene by any suitable method known to those of skill in the art. The ethyltoluenes formed are dehydrogenated by vaporizing the hydrocarbons by means of heat exchangers, passing a stream of the vapors into admixture with steam to form a vapor mixture comprising from 1 to 10, advantageously from 2 to 3 parts by weight of steam per part of hydrocarbons, and passing the vapor mixture into a reactor containing a solid, granular dehydrogenation catalyst at a reaction temperature between 550° and 700° C., preferably between 560° and 650° C. Any of the known catalysts which are suitable for use in dehydrogenating ethyltoluene may be used. A considerable number and variety of such catalysts are known and are commercially available. Catalysts of the self-regenerative type are preferably used.

A vapor mixture containing steam and vinyltoluene then leaves the dehydrogenation reactor and passes through one or more heat exchangers. A polymerization inhibitor is then injected into the vaporous mixture. Any of the inhibitors which are suitable for use in preventing the formation of undesirable thermal polymers in vinyltoluene and are soluble in the organic phase of the mixture may be utilized. Nitrated phenols are preferred, for example, dinitro-ortho-cresol, dinitro-para-cresol, meta-nitro-para-cresol, dinitro phenol, N-nitroso diphenyl amine, 4-halo-3,5-dinitro toluene, 3-nitro-2,5-cresotic acid and the like. The temperature of the vaporous mixture, at the time of the injection of the inhibitor, is preferably between about 200° C. and 300° C. in order to prevent rapid decomposition of the inhibitor and to assure maximum effectiveness of the inhibitor. If DNPC is utilized as an inhibitor, it is preferably added to the vaporous stream of crude vinyltoluene in amounts of between about 50-100 parts per million by weight relative to the vinyltoluene in the stream. The mixture is then cooled to condense the product, and the pH of the aqueous phase is adjusted, if necessary, to maintain the inhibitor in the organic phase. The pH needed to maintain the inhibitor in the organic phase will depend on the pKa of the inhibitor used. For instance, if DNPC is used as an inhibitor, a pH of 5.5-6.5 is sufficient to prevent the formation of the enolate anion, which is water soluble, and thus to maintain the DNPC substantially in the organic phase. Of course, if an inhibitor is selected which has a pKa different from that of DNPC, a different pH will be required to maintain the inhibitor in the organic phase of the vinyltoluene. The water collected may be recycled for use in future dehydrogenation reactions.

The dehydrogenation mixture may optionally and preferably be filtered to prevent transfer of any undesirable insoluble polymers into the distillation apparatus. Such polymers, unless removed, serve as seed polymers for the formation of large quantities of insoluble polymer in the distillation columns.

Additional polymerization inhibitor is added to the crude vinyltoluene prior to entry into the distillation apparatus in order to prevent any undesirable polymer formation during distillation of the vinyltoluene. Typically, an amount of inhibitor is added which is sufficient to raise the total concentration of the inhibitor to a level of about 500 parts per million by weight relative to the vinyltoluene. This has been found to be sufficient to prevent the formation of undesirable insoluble polymers during the distillation process.

The dehydrogenation mixture is fractionally distilled in a series of fractionating columns. The distillation is preferably conducted under reduced pressure to further reduce the tendency of the vinyltoluene to polymerize. Lower boiling portions are separated from the vinyltoluene. The vinyltoluene is then removed from the heavier boiling fractions. Typical operating conditions for the distillation process include a temperature from about 65° to about 138° C., and a subatmospheric pressure from about 10 to about 200 mm Hg absolute. The specific operating conditions produce a final product of commercial grade vinyltoluene which satisfies industry standards for quality and purity.

Referring to the drawings, FIG. 1 illustrates one embodiment for carrying out the process of the present invention. An ethyltoluene feed stock is introduced into a dehydrogenation apparatus 10 to form vinyltoluene. The vinyltoluene feed stock is injected with a polymerization inhibitor 12 immediately prior to condensing the vinyltoluene. The vinyltoluene feed stock is condensed in a condenser 14, then transferred via line 16 to crude vinyltoluene drum 18. The condenser 14 may comprise a condenser using a fan or water for cooling. Alternatively, any condenser suitable for condensing vaporous crude vinyltoluene may be utilized. The inhibitor 12 is preferably added as close to the quench nozzle of the condensing apparatus as possible in order to prevent decomposition of the inhibitor and to prevent the formation of undesirable polymers in the condenser 14 or the drum 18. The pH of the aqueous phase is adjusted to a pH which is sufficiently acidic to substantially maintain the inhibitor in the organic phase of the vinyltoluene feed stock.

A convenient means of controlling the pH of the aqueous phase in the crude drum comprises the following arrangement. Preferably, a partial stream of quench water is recycled from the crude drum to the condensing apparatus. A pH probe 19 is located in this recycle line, and downstream of the probe an inlet nozzle is provided for selectively injecting a pH control agent 20 when necessary. In order to maintain the aqueous phase slightly acidic, it is preferred to selectively add an inorganic mineral acid to the recycle stream, most preferably hydrochloric or sulfuric acid.

The aqueous phase of the feed stock is withdrawn from the crude vinyltoluene drum through line 21 and is recycled for water treatment and use in the boilers used in the dehydrogenation of ethyltoluene.

The product reamining in the vinyltoluene drum 18 is pumped through line 22 via pump 24 through filter 26 into a conventional vinyltoluene distillation train. Additional inhibitor 28 is injected into the vinyltoluene feed stock in line 30 in order to ensure the presence of a sufficient amount of inhibitor during the distillation process.

In this embodiment, the vinyltoluene feed stock is introduced into the intermediate portion of recycle column 32 which is preferably of the parallel distillation path design. Reboiler 34 provides the necessary heat for distillation in column 32.

An overhead product comprising toluene and ethyltoluene is withdrawn through line 35 for subsequent fractionation in distillation column 36. In column 36, toluene and other light distillates are withdrawn through line 39. An ethyltoluene bottoms product is withdrawn through line 40 and is recycled for use in the ethyltoluene dehydrogenation reactor 10. Reboiler 42 provides the bottoms with the necessary heat for the distillation.

The recycle bottoms product, containing vinyltoluene, inhibitor and polyvinyltoluene is withdrawn from the recycle column 32 through 44 using pump 46 and is charged into the middle portion of finishing column 48. A reboiler circuit comprising a reboiler 50 and an air feed line 52 is attached to the finishing column 48 for supplying the necessary heat and for establishing a counter-flow of air within the column. The purified vinyltoluene overhead product is withdrawn through line 54.

The finishing column bottoms product is directed to flash pot 56 via line 58 and pump 60. The flash pot 56 has a reboiler 62 to facilitate the fractionation of the bottoms. The tar produced during the distillation process is withdrawn through line 64 by pump 66 for proper disposal.

Figure 2:
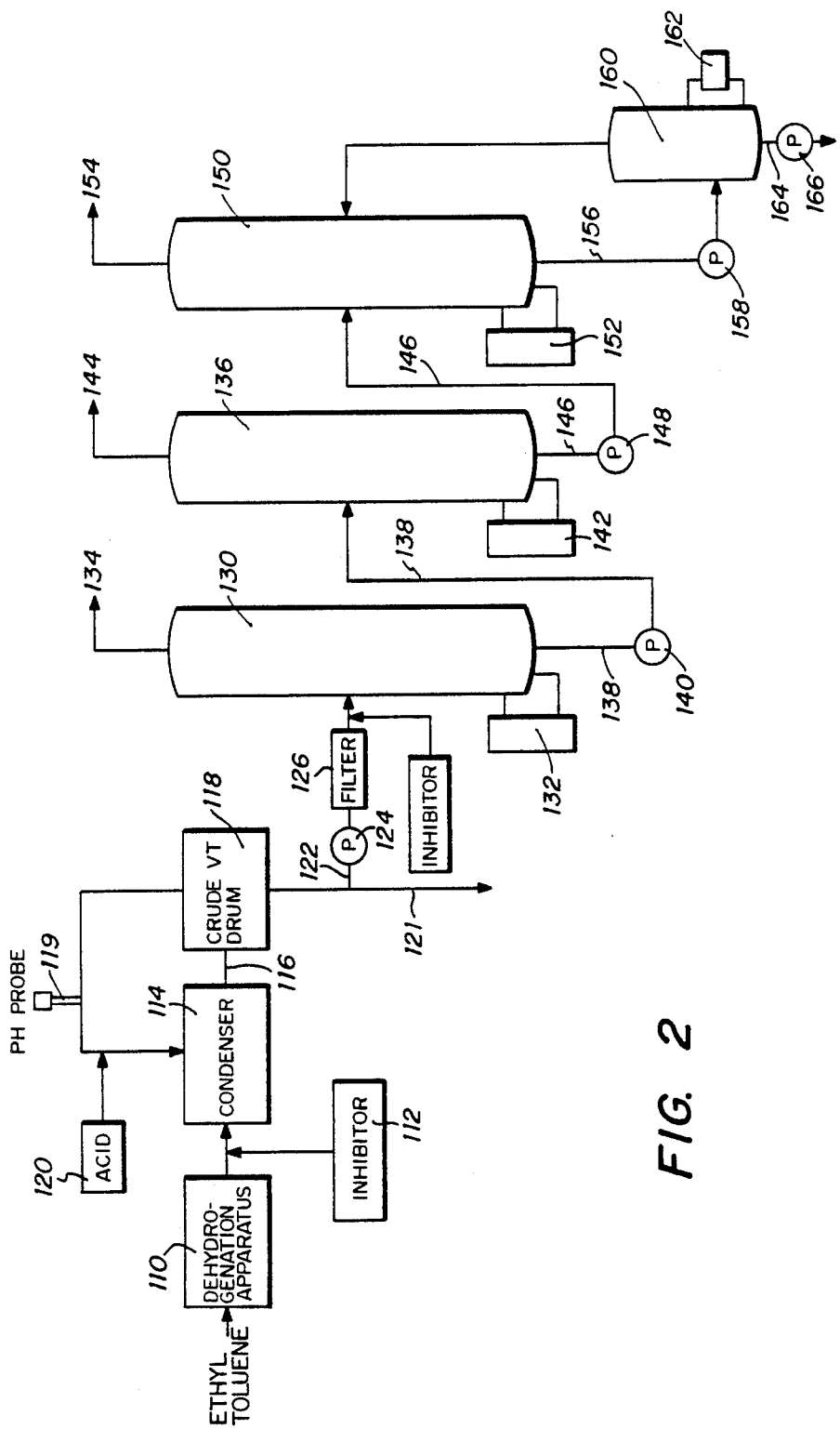
FIG. 2 shows a schematic diagram of another apparatus which may be employed in practicing the invention.

FIG. 2 illustrates the application of the process of the present invention to another distillation train for vinyltoluene. An ethyltoluene feed stock is introduced into a dehydrogenation apparatus 110 to form vinyltoluene. The vinyltoluene feed stock is injected with a polymerization inhibitor 112 prior to the condensation of the vinyltoluene as explained in connection with FIG. 1. The vinyltoluene feed stock is then condensed in condenser 114, and the condensed vinyltoluene flows via line 116 to a crude vinyltoluene drum 118. The pH of the aqueous phase is regulated by means of pH probe 119 and acid 120 as explained in connection with FIG. 1. The aqueous phase of the feed stock is withdrawn through line 121 and is recycled back to the dehydrogenation apparatus 110. The product remaining in the crude vinyltoluene drum 118 is pumped through line 122 via pump 124 through filter 126 into the vinyltoluene distillation train. Additional inhibitor 128 is added through line 122 into the vinyltoluene feed stock as explained in connection with FIG. 1.

The vinyltoluene feed stock is introduced into the intermediate portion of column 130 through feed line 122. The column 130 may be of any suitable design known to those skilled in the art and may contain any suitable number of vapor-liquid contracting devices, such as a sufficient number of bubble cap trays, perforated trays, valve trays, etc., to separate lower boiling fractions frim vinyltoluene. Alternatively, a packed column may be utilized to effect the separation. Column 130 is also equipped with a suitable reboiler 132 for supplying heat thereto.

Under the distillation conditions imposed in column 130, an overhead stream of low-boiling hydrocarbons comprising mainly toluene is removed from column 130 via line 134. These low-boiling hydrocarbons are subsequently condensed and passed into storage for further use. The bottoms product of the column 130 is then introduced into the recycle column 136 by means for line 138 and pump 140.

The recycle column 136 may be of any suitable design known to those skilled in the art. In one embodiment, the recycle column is of the parallel path design, i.e., two parallel distillation paths descending through the column. In this embodiment, it is necessary that the recycle column contain a sufficiently large number of trays to permit a proper separation between the similar boiling vinyltoluene and ethyltoluene. Alternatively, the recycle column 136 may comprise a packed column. The recycle column 136 is equipped with a suitable reboiler 142.

The ethyltoluene overhead product of the recycle column 136 is withdrawn through line 144 and is subsequently condensed for reuse in the ethyltoluene dehydrogenation apparatus 110. The recycle bottoms is withdrawn from the recycle column 136 through line 146. The recycle bottoms product is fed by pump 148 into finishing column 150 via line 146. The finishing column 150 is equipped with a reboiler 152. Inhibitor protection is adequately provided in this column and the recycle column 136 because of the prior addition of the polymerization inhibitor.

The purified vinyltoluene overhead product is withdrawn through line 154 from the finishing column. The purified vinyltoluene product will comprise commercial quality vinyltoluene. The finishing column bottoms product is withdrawn through line 156 via pump 158 into flash pot 160. The flash pot 160 has a reboiler 162 to facilitate the fractionation of the bottoms. The tar produced during the distillation process is withdrawn through line 164 by pump 166 for proper disposal. However, recycling these inhibitor-bearing tars into the recycle column is also contemplated as an optional step.

The use of the process of the present invention enables an apparatus for the production of vinyltoluene to operate at an increased rate and significantly reduces the amount of unwanted thermal polymerization normally occurring during the production of vinyltoluene.

The invention will now be further illustrated by the following non-limiting examples.

EXAMPLE I

Following several vinyltoluene production runs during which insoluble popcorn-type polymer accumulated regularly (i.e., every 1 to 3 weeks) in the primary condenser system and the crude vinyltoluene drum, a mechanism for injecting a solution of DNPC just upstream of the quench nozzle was installed. It was found that 100 ppm DNPC relative to the vinyltoluene present was effective in controlling the fouling problem caused by polymer accumulation. Utilizing the DNPC injection just prior to the quench nozzle, as described, the system has operated more than sixty days without the occurrence of significant fouling.

EXAMPLE II

Because of the ability of even vary small amounts of popcorn (insoluble) polymer to serve as seed for accumulations of additional insoluble polymer, a filter system was installed between the crude vinyltoluene drum and the distillation train of the system of Example I to prevent the forward transfer of solids. The filter system has been found to successfully accumulate the limited amounts of popcorn which remain notwithstanding the injection of the inhibitor just prior to the quench nozzle. As a consequence, the transfer of seed polymer into the distillation train has been precluded, resulting in a significant decrease in the rate of accumulation of insoluble polymer therein.

While the invention has been described in terms of various embodiments and illustrated by specific examples, various modifications, substitutions and changes can be made without departing from the spirit of the invention. Accordingly, it is intended that the scope of the present invention be ascertained solely with reference to the following claims.

What is claimed is:

1. An apparatus for manufacturing vinyltoluene comprising:
   means for dehydrogenating ethyltoluene to form vaporous vinyltoluene;
   first means for introducing a polymerization inhibitor into said vaporous vinyltoluene after said vaporous vinyltoluene leaves said dehydrogenation means;
   means for condensing said vaporous vinyltoluene to produce an aqueous crude vinyltoluene feed stock, said first inhibitor introducing means is located immediately upstream of said condensing means;
   means for adjusting the pH value of the aqueous phase of the condensed crude vinyltoluene feed stock to maintain said polymerization inhibitor in the organic phase of the condensed crude vinyltoluene feed stock;
   means for collecting said condensed crude vinyltoluene feed stock;
   a second means for introducing a polymerization inhibitor into said collected crude vinyltoluene feed stock; and
   means for purifying said vinyltoluene.

2. The apparatus of claim 1, further comprising means for filtering said vinyltoluene prior to the purification thereof.

3. Apparatus according to claim 2, wherein said filtering means comprises a filter with passages not greater than 50 microns.

4. The apparatus of claim 1, wherein said purifying means is a distillation apparatus.

5. Apparatus according to claim 4, wherein said distillation apparatus comprises a multi-column distillation train.

6. Apparatus according to claim 1, wherein said dehydrogenating means comprises a dehydrogenation reactor containing a solid, granular dehydrogenation catalyst, means for introducing an admixture comprising vaporized ethylbenzene and steam into said reactor, and means for withdrawing a vapor mixture comprising crude vinyltoluene and steam from said reactor.

7. Apparatus according to claim 1, wherein said first inhibitor introducing means comprises a source of dinitro-para-cresol solution and an injector for injecting dinitro-para-cresol solution from said source into said vaporous vinyltoluene.

8. Apparatus according to claim 1, wherein said condensing means comprises a quench nozzle for injecting an aqueous quench liquid into said vaporous vinyltoluene.

9. Apparatus according to claim 8, wherein said collecting means comprises a crude vinyltoluene drum wherein aqueous crude vinyltoluene separates into an organic phase and an aqueous phase and means for separately withdrawing said aqueous phase from said crude vinyltoluene drum.

10. Apparatus according to claim 9, further comprising means for recycling a portion of the separately withdrawn aqueous phase to a boiler for producing steam for said dehydrogenation means.

11. Apparatus according to claim 9, further comprising a quench recycle line for conveying a portion of said aqueous phase from said drum to said quench nozzle for quenching the vaporous vinyltoluene entering said condensing means.

12. Apparatus according to claim 11, wherein said pH adjusting means comprises a pH probe on said quench recycle line for measuring the pH value of the aqueous phase from said crude vinyltoluene drum and means for selectively introducing an acid into the recycle quench liquid as needed in response to the measured pH value to maintain the pH of the aqueous phase at a desired value.

13. Apparatus according to claim 1, further comprising at least one heat exchanger interposed between said dehydrogenating means and said first inhibitor introducing means for cooling said vaporous vinyltoluene prior to the first introduction of polymerization inhibitor.

14. Apparatus according to claim 1, wherein said second inhibitor introducing means comprises a source of dinitro-para-cresol solution and an injector interposed between said collecting means and said purifying means for injecting dintro-para-cresol solution from said source into the crude vinyltoluene.

* * * * *